US008158379B2

(12) United States Patent
Ronholdt (10) Patent No.: US 8,158,379 B2
(45) Date of Patent: Apr. 17, 2012

(54) METHODS FOR DETERMINING MICROBIAL CONTAMINATION OF ALLOGRAFT PRODUCTS

(75) Inventor: Chad Ronholdt, Ft. Collins, CO (US)

(73) Assignee: Allosource, Centennial, CO (US)

( * ) Notice: Subject to any disclaimer, the term of this patent is extended or adjusted under 35 U.S.C. 154(b) by 938 days.

(21) Appl. No.: 10/976,078

(22) Filed: Oct. 28, 2004

(65) Prior Publication Data

US 2005/0214895 A1 Sep. 29, 2005

Related U.S. Application Data

(60) Provisional application No. 60/515,025, filed on Oct. 28, 2003, provisional application No. 60/562,746, filed on Apr. 16, 2004.

(51) Int. Cl.
*C12Q 1/04* (2006.01)
*C12Q 1/02* (2006.01)
*C12Q 1/00* (2006.01)

(52) U.S. Cl. ............... 435/34; 435/30; 435/31; 435/32

(58) Field of Classification Search .................. None
See application file for complete search history.

(56) References Cited

U.S. PATENT DOCUMENTS

| | | | |
|---|---|---|---|
| 3,937,236 A * | 2/1976 | Runnells ............... | 134/184 |
| 4,448,750 A | 5/1984 | Fuesting | |
| 4,591,485 A | 5/1986 | Olsen et al. | |
| 4,710,233 A | 12/1987 | Hohmann et al. | |
| 4,874,137 A | 10/1989 | Chiba | |
| 5,095,925 A | 3/1992 | Elledge et al. | |
| 5,113,881 A | 5/1992 | Lin et al. | |
| 5,202,262 A | 4/1993 | Lemonnier | |
| 5,346,829 A | 9/1994 | Alspector | |
| 5,368,171 A | 11/1994 | Jackson | |
| 5,429,810 A | 7/1995 | Knaepler et al. | |
| 5,509,968 A | 4/1996 | Carr | |
| 5,556,379 A | 9/1996 | Wolfinbarger | |
| 5,591,398 A | 1/1997 | Knaepler et al. | |
| 5,607,476 A | 3/1997 | Prewett et al. | |
| 5,711,946 A * | 1/1998 | Chand-Goyal et al. .... | 424/93.51 |
| 5,716,525 A | 2/1998 | Nickerson | |
| 5,763,264 A | 6/1998 | Alspector | |
| 5,797,871 A * | 8/1998 | Wolfinbarger, Jr. ........... | 604/500 |
| 5,820,581 A | 10/1998 | Wolfinbarger, Jr. | |
| 5,927,304 A | 7/1999 | Wen | |
| 5,931,969 A | 8/1999 | Carpentier et al. | |
| 5,976,104 A | 11/1999 | Wolfinbarger, Jr. | |
| 5,977,034 A | 11/1999 | Wolfinbarger, Jr. | |
| 6,004,438 A | 12/1999 | Woodson | |
| 6,024,735 A | 2/2000 | Wolfinbarger, Jr. | |
| 6,090,572 A | 7/2000 | Crosby | |
| 6,284,875 B1 | 9/2001 | Turpen et al. | |
| 6,287,387 B1 | 9/2001 | Lee et al. | |
| 6,291,180 B1 | 9/2001 | Chu | |
| 6,326,190 B1 | 12/2001 | Ceri et al. | |
| 6,428,746 B1 | 8/2002 | Muscarella et al. | |
| 6,428,975 B1 | 8/2002 | Brinkley | |
| 6,482,584 B1 | 11/2002 | Mills et al. | |
| 6,506,584 B1 | 1/2003 | Chandler et al. | |
| 6,652,818 B1 | 11/2003 | Mills et al. | |
| 2003/0027125 A1 | 2/2003 | Mills et al. | |
| 2004/0037735 A1 | 2/2004 | DePaula et al. | |

FOREIGN PATENT DOCUMENTS

| | | |
|---|---|---|
| DE | 101 04 558 C 1 | 6/2002 |
| GB | 2 350 106 A | 11/2000 |
| WO | WO 0029037 A1 * | 5/2000 |

OTHER PUBLICATIONS

Lomas et al, "Processing of whole femoral head allografts: A method for improving clinical efficacy and safety," (Cell and Tissue Banking), vol. 1, 2000, pp. 193-200.*
Farrington et al, "Microbiological monitoring of bone grafts: two years' experience at a tissue bank," (Journal of Hospital Infection), vol. 38, 1998, pp. 261-271.*
Bobbitt et al. "The removal of bacteria from solutions by membrane filtration", Journal of Microbiological Methods, 1992, vol. 16, pp. 215-220.*
Yrios, et al., "Survival of Anaerobic and Aerobic Bacteria on Cotton Swabs in Three Transport Systems" (Feb. 1975), *Journal of Clinical Microbiology*, vol. 1, No. 2, pp. 196-200.
Gristina, et al., "Bacterial Adherence to Biomaterials and Tissue" (Feb. 1985), *The Journal of Bone and Joint Surgery, Incorporated*, vol. 67-A, No. 2, pp. 264-273.
Padberg, Jr. et al., "Optimal Method for Culturing Vascular Prosthetic Grafts" (Oct. 1992), *Journal of Surgical Research*, vol. 53, No. 4, pp. 384-390.
Gorman, et al., "Incidence and nature of peritoneal catheter biofilm determined by electron and confocal laser scanning microscopy" (1994), *Epidemiol. Infect.*, vol. 112, pp. 551-559.
Veen, et al., "Sensitivity and Negative Predictive Value of Swab Cultures in Musculoskeletal Allograft Procurement" (Mar. 1994), *Clinical Orthopaedics and Related Research*, vol. 300, pp. 259-263.
Padberg, Jr., et al., "Accuracy of Disincorporation for Identification of Vascular Graft Infection" (Feb. 1995), *Arch. Surg.*, vol. 130, pp. 183-187.

(Continued)

*Primary Examiner* — Laura Schuberg
(74) *Attorney, Agent, or Firm* — Sheridan Law, LLC (57) ABSTRACT

A method for determining microbial contamination of allograft products includes providing an extraction vessel having an outer container and a removable inner basket, placing the allograft product into the inner basket, providing an extraction fluid in the outer container of the extraction vessel, positioning the inner basket in the outer container, so that the allograft product and the inner basket are submerged in the extraction fluid and agitating the extraction fluid for a predetermined amount of time and analyzing the extraction fluid for microbial contamination.

21 Claims, 6 Drawing Sheets

OTHER PUBLICATIONS

Tunney, et al. "Improved detection of infection in hip replacements" (Jul. 1998), *The Journal of Bone and Joint Surgery*, vol. 80-B, pp. 568-572.

Farrington, et al., "Microbiological monitoring of bone grafts: two years' experience at a tissue bank" (1998), *Journal of Hospital Infection*, vol. 38, pp. 261-271.

Vehmeyer, et al., "A comparative study of blood and bone marrow cultures in cadaveric bone donation" (1999), *Journal of Hospital Infection*, vol. 43, pp. 305-308.

Roelofsen, et al., "Evaluation of the Effects of Storage in Two Different Swab Fabrics and under Three Different Transport Conditions on Recovery of Aerobic and Anaerobic Bacteria" (Sep. 1999), *Journal of Clinical Microbiology*, vol. 37, No. 9, pp. 3041-3043.

Tunney, et al., "Detection of Prosthetic Hip Infection at Revision Arthroplasty by Immunofluorescence Microscopy and PCR Amplification of the Bacterial 165 rRNA Gene" (Oct. 1999), *Journal of Clinical Microbiology*, vol. 37, No. 10, pp. 3281-3290.

Lomoas, et al., "Processing of whole femoral head allografts: A method for improving clinical efficacy and safety" (2000), *Cell and Tissue Banking*, vol. 1, pp. 193-200.

Vehmeyer, et al., "Microbiological screening of post-mortem bone donors—two case reports" (2001), *Journal of Hospital Infection*, vol. 47, pp. 193-197.

Nguyen, et al., "Detecting Bacterial Colonization of Implanted Orthopaedic Devices by Ultrasonication" (Oct. 2002), *Clinical Orthopaedics and Related Research*, vol. 403, pp. 29-37.

Fuchs, "Ultrasonic Cleaning: Fundamental Theory and Application" (Revised May 2002), *Blackstone-Ney Ultrasonics*, pp. 1-14.

Rodrigo, et al., "Intelligent Ultrasonics for the Disk Drive Industry" (Sep. 2000), *A2C2 Magazine*, pp. 1-4, http://www.a2c2.com/articles/00sept_044.asp?pid=86&articleText=00sept_044, date visited—Apr. 15, 2004.

Mills et al., "Evaluation of Culturing Methods at Predicting Allograft Sterility for Aseptically Processed Tissue", Aug. 25-29, 2001, Poster and Abstract from 25th Annual Meeting of American Association of Tissue Banks, Washington, DC.

Man et al., "Evidence of bacterial biofilm in tubing from hydraulic pathway of hemodialysis system", Abstract from PubMed, Artif Organs Jul. 1998; 22 (7): pp. 596-600.

Wengrovitz, et al., "Sonication provides maximal recovery of *Staphylococcus epidermis* from slime-coated vascular prosthetics", Abstract from PubMed, Am Surg Mar. 1991; 57(3):161-4.

"Ultrasonic Energy Meter", *ppb, Inc.*, http://www.megasonics.com/map.html, date visited—Apr. 15, 2004.

WPI/Thomson Abstract of Japanese Patent No. 200217596, Abstract Only.

\* cited by examiner

METHODS FOR DETERMINING MICROBIAL CONTAMINATION OF ALLOGRAFT PRODUCTS

RELATED APPLICATIONS

This application claims the benefit of U.S. Provisional Application No. 60/515,025, filed Oct. 28, 2003 and U.S. Provisional Application No. 60/562,746, filed Apr. 16, 2004. The entire disclosures of which are hereby incorporated by reference.

TECHNICAL FIELD

The present invention relates generally to methods for detecting microbial contamination of products, and more specifically to a unique method for detecting microbial contamination of allograft products.

BACKGROUND OF THE INVENTION

The use of musculoskeletal allograft tissue in reconstructive orthopedic procedures and other medical procedures has markedly increased over the last decade. Over the past decade, more than five million musculoskeletal allografts have been safely transplanted. The most common allograft is bone. However, tendons, skin, heart valves and corneas are other common types of tissue allografts.

Prior to use, the allograft tissue must be evaluated for microbial contamination. The allograft product must be tested for bacterial contamination prior to release of the tissue for transplantation. Swabs are widely used in the pharmaceutical and medical device industry for evaluating microbial contaminants on small, hard, non-porous manufacturing equipment, in addition to detecting microbial contaminants in environmental monitoring programs. In the clinical setting, swabs are primarily used to diagnose clinical diseases. The use of swabs was adopted by the tissue banking industry several years ago for detecting microbial contamination. Swabs are used on porous, freeze-dried and frozen allograft products. It is not an uncommon perception that swabs are not all that sensitive or reproducible when detecting microbial contamination from various surfaces. The ability of the swab to recover contaminant microorganisms is dependent on two events; the first is its ability to "pick-up" viable contaminants from the surface of the article being swabbed and the second event, is the "release" of any microbial contaminants from the swab into an appropriate growth environment (e.g. solid agar medium or broth). In addition, on some allografts, the swab is not capable of contacting the entire surface area of the allograft. Moreover, some areas of the allograft are simply inaccessible to a swab, thereby not allowing for complete analysis of the allograft for microbial contaminants.

Another method used for detecting microbial contamination on allografts is destructive testing. Destructive testing using companion tissues (small sections of typically lower quality or unusable portions of the allograft) is routinely used to assess microbial contamination on entire allograft lots. This practice has come under intense scrutiny by regulatory agencies since the companion tissue may not be representative of the microbial contamination on entire allograft lot. Furthermore, the geometry of the companion tissue does not adequately represent the geometry of the entire allograft lot.

Recently, non-allograft materials from varying sources (bovine, ceramic, synthetic, etc.) have been used as a representative model of what the allograft tissue products are exposed to during handling and processing. The limitation with these materials is that they are not truly representative of the actual allograft. Furthermore, it is extremely difficult to fabricate synthetic samples to model every product category currently utilized for transplantation.

In the past, ultrasound has been utilized to minimize and/or eliminate microbial contamination of allograft products. Ultrasound is microbiostatic to most microbes, and is used primarily to reduce microbial loads from inanimate objects with specific bacteriocidal activity on gram-negative bacteria.

With the increased use of allograft products, there is a need to provide methods with improved detection of microbial contamination of allograft products.

SUMMARY OF THE INVENTION

The present invention is directed to methods for determining microbial contamination of allograft products. The methods utilize agitation of the allograft product in an extraction fluid and subsequent analysis of the extraction fluid for microbial contamination including enumeration and identification.

One embodiment of the present invention is a method for determining microbial contamination of allograft products. The method comprises: providing an extraction vessel, wherein the extraction vessel comprises an outer container and a removable inner basket; placing the allograft product into the inner basket; providing an extraction fluid in the outer container of the extraction vessel; positioning the inner basket in the outer container, wherein the allograft product in the inner basket is submerged in the extraction fluid; agitating the extraction fluid for a predetermined amount of time; removing the inner basket containing the allograft product from the outer container; and analyzing the extraction of fluid for microbial contamination.

BRIEF DESCRIPTION OF THE DRAWINGS

While the specification concludes with claims particularly pointing and distinctly claiming the present invention, it is believed that the same will be better understood from the following description taken in conjunction with the accompanying drawings in which:

The embodiments set forth in the drawings are illustrative in nature and not intended to be limiting of the invention defined by the claims. Moreover, individual features of the drawings and the invention will be more fully apparent and understood in view of the detailed description.

DETAILED DESCRIPTION

Applicants have surprisingly found that microbial contamination of allograft products can be determined by placing the allograft products in an extraction fluid, agitating the fluid and thereafter analyzing the extraction fluid for contamination. This method has been demonstrated to be far superior to the swab technique, which is currently employed for assessing microbial contamination of allograft products. While manual agitation of the allograft products is effective, sonication (i.e., applying sound waves to the extraction fluid and the allograft products) may also be employed. Applicants have also developed an apparatus, which facilitates agitation. Astonishingly, applicants have found that allograft products can be sonicated in this apparatus at ultrasonic frequencies for long durations in order to cause any microbial contaminants present on the allograft products to be transferred to the extraction fluid, while maintaining the viability of the contaminants. In this manner, the extraction fluid can be analyzed for microbial contamination, thus providing a determination of whether or not the allograft products themselves are contaminated.

Figure 1:
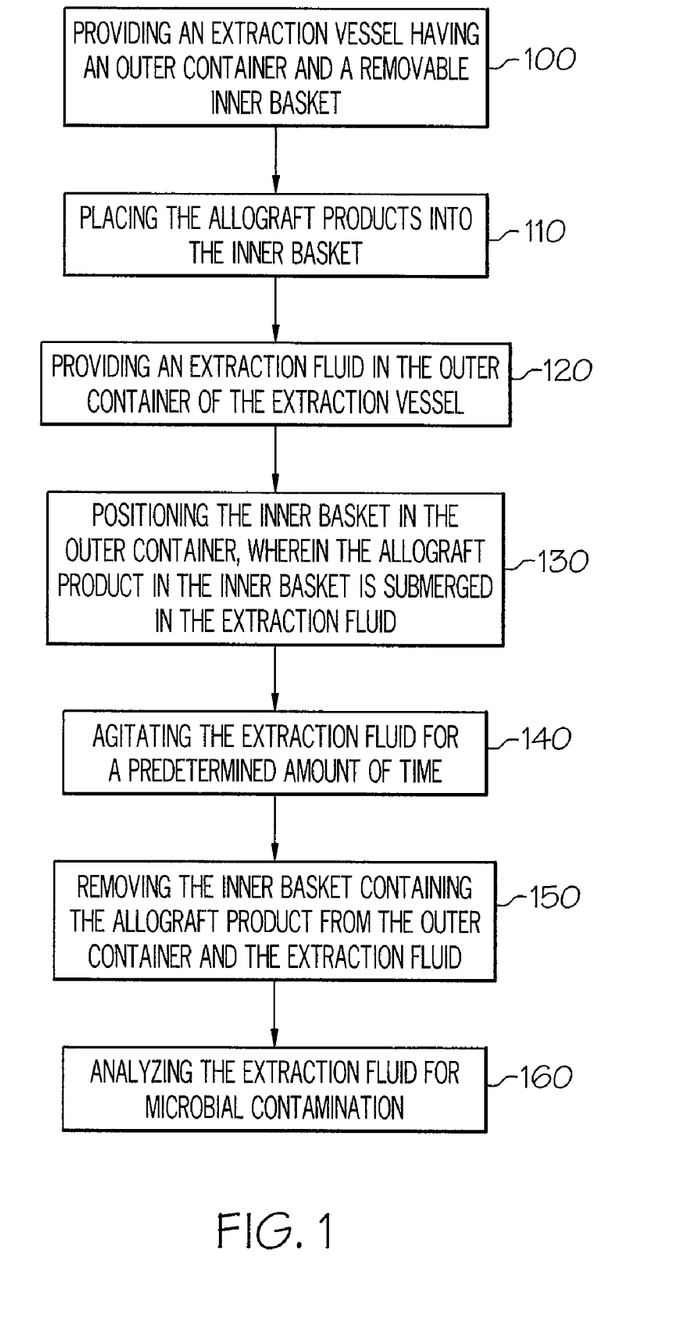
FIG. 1 is a flow diagram of an exemplary method according to an embodiment of the present invention.

FIG. 1 illustrates an exemplary method for determining microbial contamination of allograft products, wherein such a method is illustrated as steps in the flow diagram. The method comprises providing an extraction vessel having an outer container and a removable foraminous inner container or basket (100). The allograft products are placed into the inner basket (110), and an extraction fluid is provided in the outer container of the extraction vessel (120). The inner basket is positioned in the outer container such that the allograft products in the inner basket are submerged in the extraction fluid (130). The extraction fluid is agitated for a predetermined amount of time (140). Thereafter, the inner basket containing the allograft products is removed from the outer container and the extraction fluid (150), is analyzed for microbial contamination (160). In one embodiment, the inner basket is removed while the extraction fluid is being agitated. Thereafter, the extraction fluid is analyzed for contamination. For example, the extraction fluid may be cultured in order to determine if microbial contamination is present.

Figure 2A:
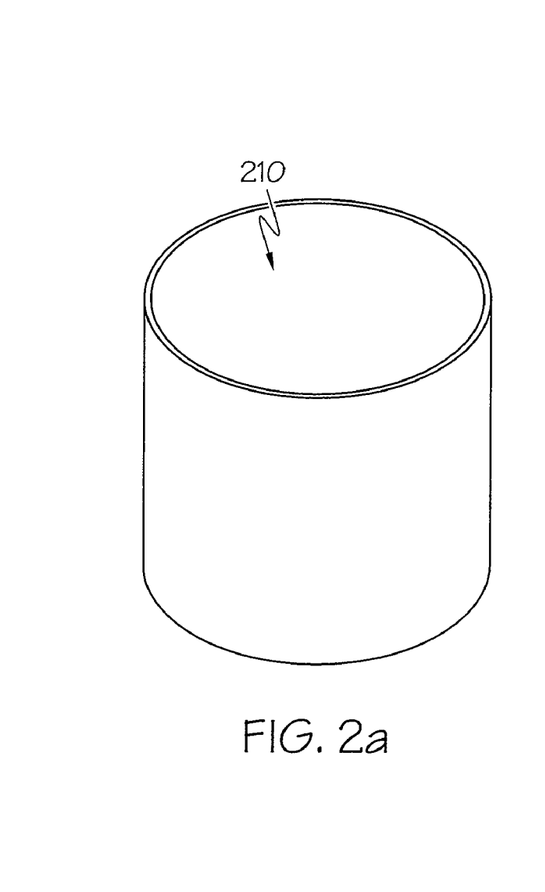
FIG. 2 is a schematic illustration of an exemplary extraction vessel of the present invention.
Figure 2B:
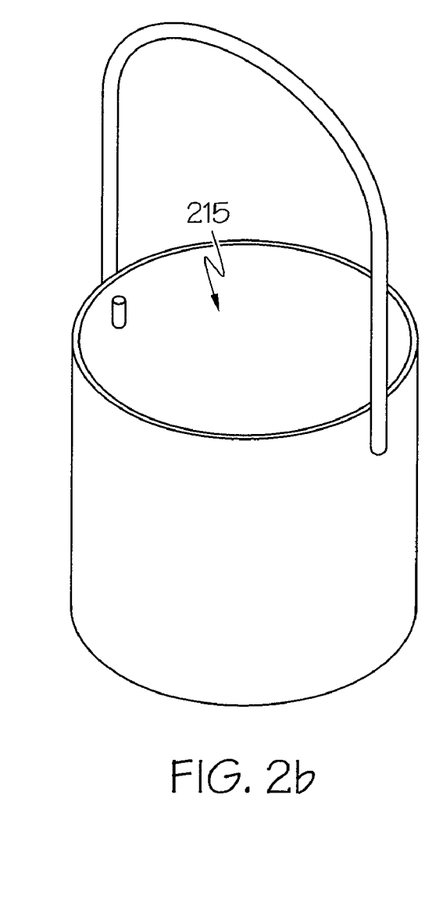

FIG. 2 illustrates an exemplary extraction vessel (200), which can be utilized with the exemplary embodiments of the present invention. The extraction vessel (200) comprises an outer container (210) and a foraminous inner basket (215). The inner basket (215) is configured to fit within the outer container (210) of the extraction vessel (200). At least some portion of the inner basket (215) is configured to allow the extraction fluid to contact the allograft products when the inner basket is submerged in the extraction fluid and to allow the extraction fluid to drain from the allograft product and inner basket when the inner basket is removed from the extraction fluid in the outer container. In one embodiment, the outer container (210) is constructed from stainless steel. Alternative materials of construction could comprise Delrin™ acetal resin from DuPont; PEEK (polyetheretherketone) resin; polycarbonate; and other resins known to one skilled in the art. The alternative materials utilized may have reduced costs, limit microbial adherence to the extraction vessel and aid in the fabrication of multiple sizes of the extraction vessel. The inner basket (215) of the extraction vessel (200) may be constructed of stainless steel. In another embodiment, the inner basket (215) may comprise a stainless steel mesh bag, which will allow smaller sized allograft products to be examined for possible microbial contamination. In one embodiment, the materials of construction for the inner basket (215) comprise the same materials of construction as the outer container of the extraction vessel (200).

In one embodiment of the present invention, the agitation of the extraction fluid comprises manual agitation. One exemplary embodiment of manual agitation of the extraction fluid comprises removing (raising) the inner basket, containing the allograft test articles, to approximately four inches above the surface of the extraction fluid in the outer container. The inner basket is allowed to completely drain of extraction fluid. The inner basket is then lower to completely resubmerge the allograft test articles again. The extraction fluid level in the outer container is sufficient to cover all of the test articles when the inner basket is submerged in the outer container. This manual agitation method is repeated for two minutes or approximately about 32 to about 40 "dunks". Following the two-minute agitation cycle, the test articles are removed from the extraction vessel and the extraction fluid is processed via filtration for microbial enumeration and identification.

Figure 3:
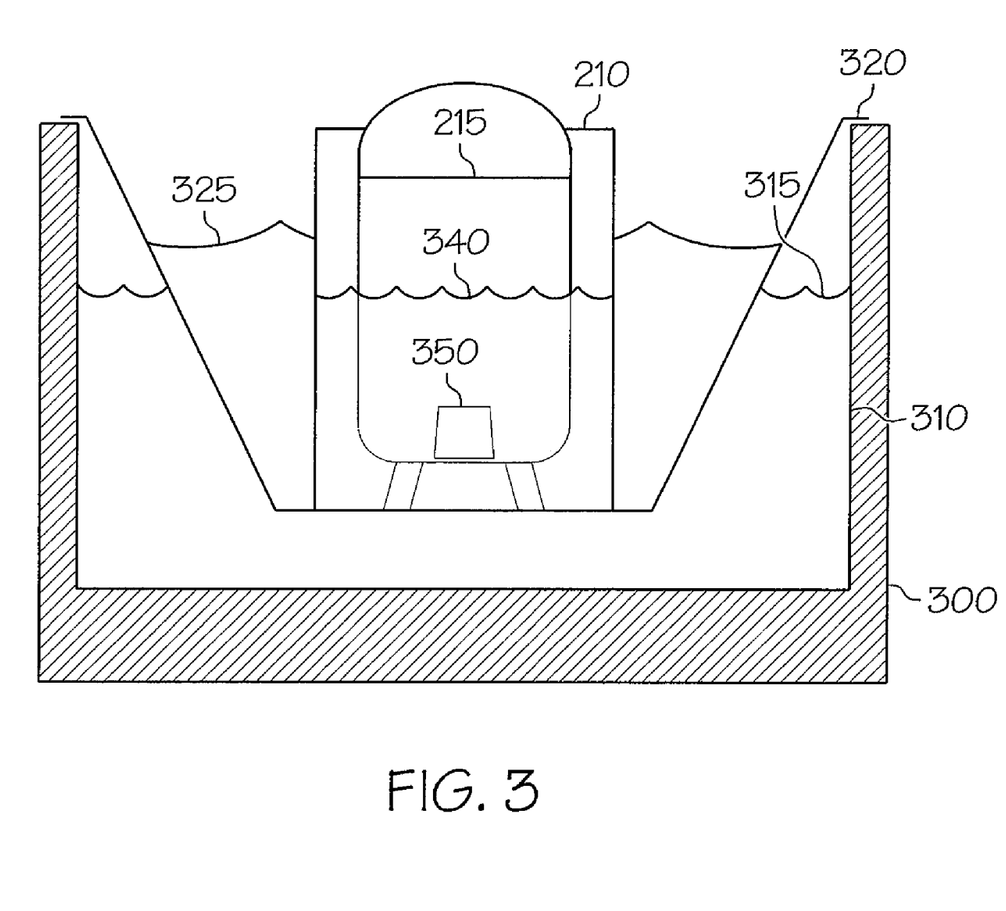
FIG. 3 is a schematic illustration of an exemplary sonication unit of the present invention.

In another exemplary embodiment, the extraction fluid is sonicated. FIG. 3 illustrates an exemplary sonication unit (300), which can be utilized. The use of ultrasonic energy allows for a much more standardized and consistent agitation step. The exemplary sonication unit (300) has a sonication bath (310) comprising a first fluid (315). A sonication chamber (320) having a second fluid (325) therein is set in the sonication bath (310). The sonication chamber (320) is configured to receive the outer container (210). The sonication chamber (320) is positioned at least partially within the first fluid (315) of the sonication bath (310). The outer container (210) is positioned within the sonication chamber (320), such that the level of the second fluid (325) is greater than the level of the extraction fluid (340) within the outer container (210). The product (350) is placed inside the inner basket (215) and ultrasonic energy is applied to the first fluid (315) in the sonication bath (310) such that the extraction fluid (340) within the outer container (210) is indirectly sonicated. In one exemplary embodiment the first fluid (315) and the second fluid (325) comprise sterile deionized water.

In one embodiment of the present invention, the extraction fluid in which the allograft(s) is immersed is sonicated for at least about one minute, at a frequency of at least about 39 kHz. In some embodiments, it may be appropriate to sonicate the extraction fluid for between about 1 and about 45 minutes, and/or sonicate at a frequency of between about 39 kHz and about 1 MHz. In an alternative embodiment, the extraction fluid is sonicated at a frequency ranging from about 39 kHz to about 172 kHz. In yet another alternative embodiment, the extraction fluid is sonicated at a frequency of about 104 kHz. It may also be desirable in some embodiments to sonicate at an intensity of at least about 50 Watts per gallon, in other embodiments sonication may be conducted at an intensity of between about 50 and about 200 Watts per gallon. In an alternative embodiment, the extraction fluid is sonicated at an intensity ranging from about 100 to about 550 Watts per gallon. In yet another alternative embodiment, sonication may be conducted at an intensity ranging from about 200 to about 400 Watts per gallon. As shown in the exemplary embodiment of FIG. 3, when the extraction fluid is sonicated in a sonication bath, it may be desirable to ensure that the allografts are not in contact with the walls of the sonication bath itself (310 in FIG. 3). As seen in FIG. 3, the allografts are positioned above (spaced-away from) the bottom sonication bath 310 in order to ensure sufficient sonication of the extraction fluid surrounding the allografts (i.e., avoid "dead zones"). Sonication, in an exemplary embodiment, may be conducted at a temperature of between about 4° C. and about 40° C.

In another embodiment of the present invention, other single frequencies or combinations of cyclical or pulsed frequencies may offer advantages with respect to microorganism recoveries. For example, the extraction fluid may be sonicated at multiple frequencies for different periods of time in order to ensure adequate recovery of microorganisms (e.g., $X^1$ minutes at $N^1$ kHz, $X^2$ minutes at $N^2$ kHz, etc.).

Other exemplary methods of agitating the extraction fluid and/or the allograft test products include, but are not limited to, the use of mechanical unit, which vigorously shake the allograft products, orbital shaker, and/or vortexing table or vigorously stirs the extraction fluid surrounding the allograft proudcts.

In one exemplary embodiment, the method of the present invention further comprises filtering the extraction fluid before analyzing the extraction fluid for microbial contamination. Exemplary filter membrane sizes range from about 0.10 µm to about 1.0 µm. One exemplary filter comprises a 0.22 µm PALL Supor™ membrane filter having a polyethersulfone membrane with a 12.25 cm² filter area operating at 635 mm Hg (25 in. Hg) of vacuum pressure. Other filters known to those skilled in the art may also be utilized which provide optimum flow rate, ease of use, microbial recoveries and are provided sterile by the manufacturer.

In one exemplary embodiment, the step of analyzing the extraction fluid for microbial contamination comprises culturing the extraction fluid or the filtrate of the extraction fluid. For example, the extraction fluid may be cultured on a solid agar medium. As one skilled in the art will appreciate, any appropriate microbial growth system may be utilized. In another embodiment, the step of analyzing the extraction fluid for microbial contamination does not comprise solely of culturing the extraction fluid, as other detection techniques may be utilized (e.g. molecular biology, radiolabeling, fluorochrome labeling, and other protein labeling techniques). In one embodiment, the samples on the agar are incubated at 22° C. for 14 days with periodic growth checks at 2, 5, 7, and 14 days. In another embodiment of the present invention, the samples are incubated at 32° C. for 14 days and periodic growth checks at 2, 5, 7, and 14 days. In one embodiment, the step of analyzing the extraction fluid comprises incubating the fluid on an agar medium from about 7 to about 14 days at a temperature of from about 4° C. to about 40° C.

The method of the present invention can also be utilized to analyze allograft products for microbial (organic) and inorganic (non-viable) contamination. In one exemplary embodiment, the extraction fluid comprises sterile water. Other exemplary extraction fluids known to one skilled in the art that help disperse and reduce the adherent properties of the microorganisms comprise one or more of the following: phosphate buffered saline solution, one or more detergents (such as Tween 80 (polyoxyethylene sorbitan monoleate), sterile Fluid D available from Millipore Corporation), and/or mixtures thereof.

In one exemplary embodiment of the present invention, the extraction fluid is at ambient temperature. In other exemplary embodiments, operation at elevated or decreased temperatures may increase microbial recoveries. In one embodiment of the present invention, the extraction fluid temperature may be between about 4° C. and about 40° C.

In one embodiment of the present invention, the extraction vessel is configured to allow complete retrieval of the extraction fluid from the extraction vessel after a product has been submerged in the inner basket in the extraction vessel.

The methods of the present invention allow analysis of all the surface area of the allograft products for microbial contamination without destroying the allograft product or diminishing the biomechanical properties of the product. Another advantage of the present method when utilizing water as the extraction fluid is the avoidance of leaving residual chemicals on a surface of the allografts and preserving the microbial integrity and viability of any microorganisms present in the fluid. The present method allows for analysis of the entire extraction fluid volume required to test the allograft products and yields a consistent, robust and reproducible method by which to assess allograft safety prior to distribution and transplantation.

EXAMPLES

Example 1

In this example, a study was performed to validate a method to detect microbial contamination on human allograft products. A total of 126 total allografts were tested. Of the 126 total allografts, 63 were soft tissue (ST) and 63 were for cut tissue (CT). The samples were each sonicated for two minutes at a frequency of 42 kHz. Spiked samples were seeded with between 63-203 CFU (colony forming units). The following microorganisms were examined: *Aspergillus niger* (AN); *Candida ablicans* (CA); *Bacillus subtilis* (BS); *Staphylococcus aureus* (SA); *Pseudomonas aeruginosa* (PA); and *Clostridium sporogenes* (CS). The test articles (TA) of this example, comprised of seeded allografts, which were examined with sonication according to one exemplary embodiment of the present invention. For comparative purposes, positive controls (PC), baseline samples (BL), inoculum check samples (IC) and negative controls (NC) were also prepared and examined. Positive controls were prepared using extraction fluid spiked with the six microorganisms and sonicated for two minutes. Baseline samples (BL) were prepared using seeded allografts, which were soaked for five minutes. Negative controls (NC) consisted of allografts that were sonicated but not seeded with microorganisms. Six test articles (TA) were prepared for each of the microorganisms. After being agitated in the extraction fluid of the extraction vessel, the sample was removed from the extraction container and the extraction fluid was filtered for each sample using a 0.22 µm filter membrane and subsequently placed onto appropriate solid agar medium. All samples were incubated at approximately 22 or 32° C., for 14 days with periodic growth checks at 2, 5, 7, and 14 days according to the appropriate USP compendial method for the selected microorganism.

Table I discloses the average extraction results (CFUs) for the soft tissue samples.

TABLE I

| SOFT TISSUE | | | | |
|---|---|---|---|---|
| | IC | PC | BL | TA |
| BS | 88 | 76 | 32 | 42 |
| CS | 125 | 111 | 51 | 59 |
| SA | 203 | 189 | 90 | 112 |
| PA | 194 | 67 | 0.3 | 1.2 |
| CA | 141 | 162 | 61 | 100 |
| AN | 98 | 62 | 48 | 54 |

Figure 4:
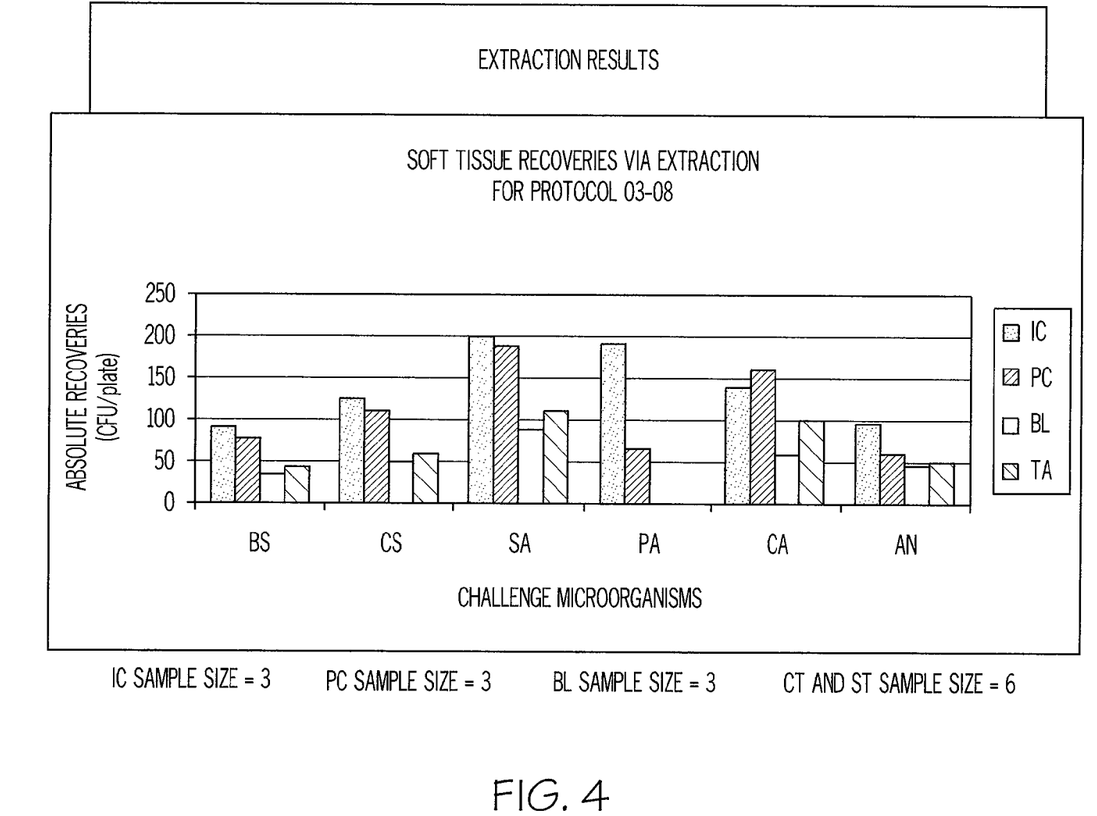
FIG. 4 sets forth soft tissue recoveries via extraction according to the present invention and comparative controls.

FIG. 4 graphically illustrates the results disclosed in Table I.

Table II discloses the average extraction results (CFUs) for the cut tissue samples.

TABLE II

| CUT TISSUE | | | | |
|---|---|---|---|---|
| | IC | PC | BL | TA |
| BS | 97 | 100 | 45 | 66 |
| CS | 108 | 145 | 60 | 72 |
| SA | 201 | 233 | 88 | 178 |

TABLE II-continued

| | CUT TISSUE | | | |
|---|---|---|---|---|
| | IC | PC | BL | TA |
| PA | 189 | 43 | 0.7 | 1.8 |
| CA | 99 | 92 | 60 | 50 |
| AN | 63 | 38 | 28 | 35 |

Figure 5:
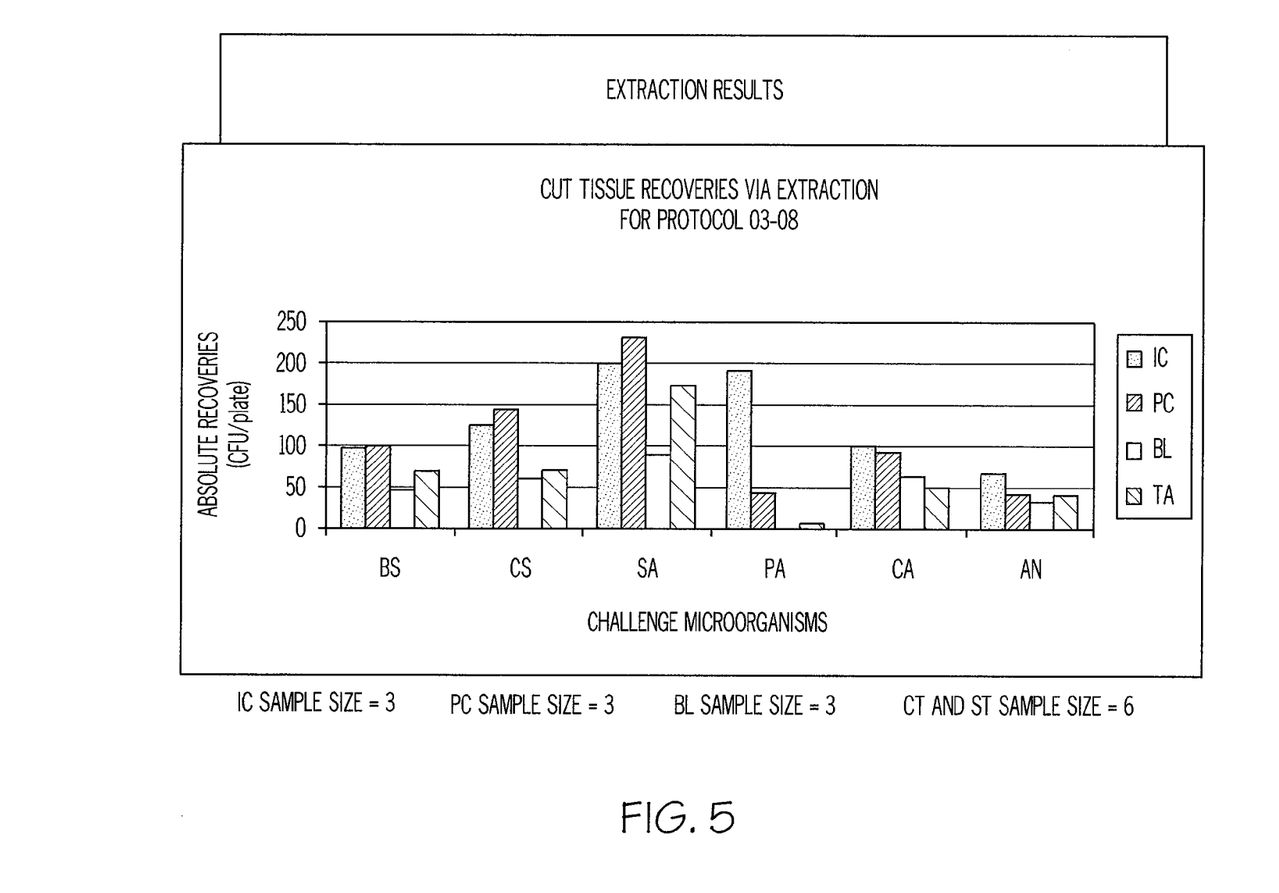
FIG. 5 sets forth cut tissue recoveries via extraction according to the present invention and comparative controls.

FIG. 5 graphically illustrates the results disclosed in Table II.

Table III discloses the percent positive for the test articles based on type of allograft (i.e., Soft Tissue or Cut Tissue) and microorganism. Percent positive is calculated by dividing the number of positives by the total number of samples.

TABLE III

| | Percent Positive (Test Articles Only) | | | | |
|---|---|---|---|---|---|
| | | Soft Tissue | | Cut Tissue | |
| | Total # of Samples | # of Positive | % Positive | # of Positive | % Positive |
| BS | 6 | 6 | 100% | 6 | 100% |
| CS | 6 | 6 | 100% | 5 | 83% |
| SA | 6 | 6 | 100% | 6 | 100% |
| PA | 6 | 3 | 50% | 5 | 83% |
| CA | 6 | 6 | 100% | 6 | 100% |
| AN | 6 | 6 | 100% | 6 | 100% |

Based upon the experimental data, all challenge microorganisms were positive at 48 hours. All samples achieved their maximum CFU count by Day 7 (i.e., no additional growth after 7 days) with one exception, CA.

Table IV discloses the percent CFU recoveries of the present example. The theoretical yield was calculated by dividing the average test article count by the average inoculum check count. The overall method capabilities were calculated by dividing the average test article count by the average positive control result. Finally, the sonication capabilities were calculated by dividing the average test article count by the average baseline result.

TABLE IV

| | | Percent CFU Recoveries | | |
|---|---|---|---|---|
| | | Theoretical Yield | Overall Method Recovery | Sonication Capabilities |
| BS | CT | 68% | 66% | 147% |
| | ST | 48% | 55% | 131% |
| CS | CT | 67% | 50% | 120% |
| | ST | 47% | 53% | 116% |
| SA | CT | 89% | 76% | 202% |
| | ST | 55% | 59% | 124% |
| PA | CT | 1% | 4% | 257% |
| | ST | 1% | 2% | 400% |
| CA | CT | 51% | 54% | 83% |
| | ST | 71% | 62% | 164% |
| AN | CT | 56% | 92% | 125% |
| | ST | 55% | 87% | 113% |

Example 2

In this comparative example, dry sampling of swabs on multiple allograft products was examined. A total of 168 total allografts were tested. Of the total allografts, 84 were soft tissue (ST) and 84 were for cut tissue (CT). Two swab methods known to those skilled in the art were examined: COPAN, COPAN Diagnostics, Corona, Calif. (CP) swabs and EZ Culturette, Becton Dickinson, Sparks, Md. (EZ) swabs. CP swabs are placed into isotonic solution and allowed to dissolve (~60 min), filtered on 0.22 μm membrane and placed on solid agar plates. EZ swabs are directly streaked onto solid agar plates by rotating the plates 120° three times. Test articles were seeded with less than 36 CFU. The following microorganism were examined: *Aspergillus niger* (AN); *Candida ablicans* (CA); *Bacillus subtilis* (BS); *Staphylococcus aureus* (SA); *Pseudomonas aeruginosa* (PA); and *Clostridium sporogenes* (CS). The test articles (TA) of this example comprised using the swap method on seeded allografts. For comparative purposes, positive controls (PC), inoculum check samples (IC) and negative controls (NC) were also prepared and examined. Positive control samples were prepared by directly inoculating the microorganism onto the swab and then applying the appropriate culturing method for each swab (shows what the swab releases). Negative controls consisted of swabs without the seeded microorganisms. All plates were incubated appropriately (~22 or ~32° C.) for 7 days with growth checks at 2 and 7 days.

Table V discloses the percent CFU recovered from the samples.

TABLE V

| | Percent CFU Recovered | |
|---|---|---|
| | Soft Tissue (% Recovered) | Cut Tissue (% Recovered) |
| BS | 12 | 0 |
| CS | 0 | 3 |
| SA | 20 | 0 |
| PA | 12 | 0 |
| CA | 23 | 2 |
| AN | 20 | 67 |
| Range | 0–23 | 0–67 |

Figure 6:
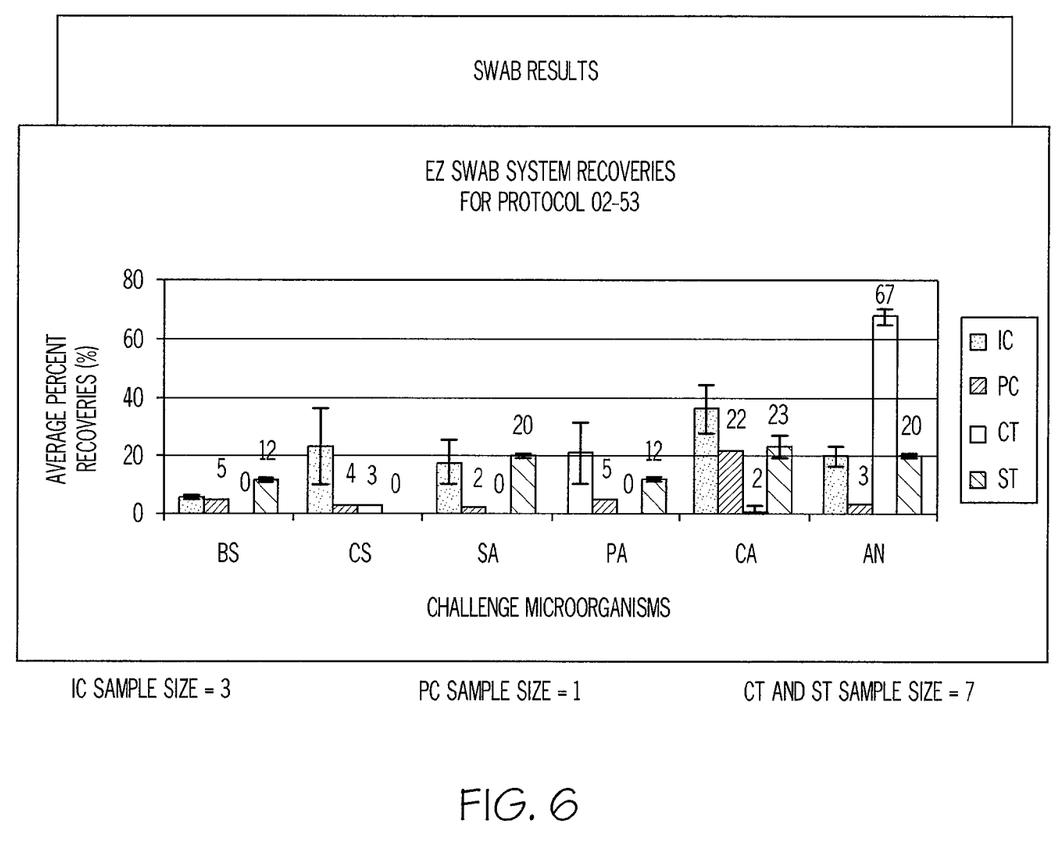
FIG. 6 sets forth recoveries via extraction according to a comparative swab method utilized in the prior art.

FIG. 6 graphically illustrates the results disclosed in Table V.

Table VI discloses the percent recovery for the test articles based on type of allograft (i.e., Soft Tissue or Cut Tissue) and microorganism. Percent positive is calculated by dividing the number of positives by the total number of samples.

TABLE VI

| | Percent Positive (Test Articles Only) | | | | |
|---|---|---|---|---|---|
| | | Soft Tissue | | Cut Tissue | |
| | Total # of Samples | # of Positive | % Positive | # of Positive | % Positive |
| BS | 7 | 3 | 43% | 0 | 0% |
| CS | 7 | 0 | 0% | 1 | 14% |
| SA | 7 | 2 | 29% | 0 | 0% |
| PA | 7 | 2 | 29% | 0 | 0% |
| CA | 7 | 6 | 86% | 1 | 14% |
| AN | 7 | 3 | 43% | 4 | 57% |

As can be seen by the above examples, the detection method of the present invention yields more accurate results for the determination of microbial contamination on allograft products and provide a much higher percent recovery and percent positive rate for each of the microorganisms. Statistical analysis of the results from Examples 1 and 2 determined that the extraction microbial detection method of the present invention (Example 1) was 108.7 times more likely to yield positive results than the prior art swab method (Example 2) regardless of the challenge microorganism.

The foregoing description of the various embodiments of the invention has been presented for the purposes of illustration and description. It is not intended to be exhaustive or limit the invention to the precise form disclosed. Many alternatives, modification and variations will be apparent to those skilled in the art of the above teaching. Accordingly, this invention is intended to embrace all alternative, modifications and variations that have been discussed herein, and others that fall within the spirit and broad scope of the claims.

I claim:

1. A method of determining contamination of a chosen allograft product, comprising:
   (a) providing an extraction fluid in a given volume sufficient to fully immerse the chosen allograft product;
   (b) immersing the chosen allograft product separate from other allograft products into said extraction fluid;
   (c) agitating said extraction fluid in which the allograft products are immersed so as to dislodge any microbial contaminants from the chosen allograft product;
   (d) removing the allograft products from said extraction fluid;
   (e) filtering an entire amount of the given volume of the extraction fluid with a filter membrane to produce an extract filtered from the entire amount of the given volume of said extraction fluid, and said extract having a higher concentration of the any microbial contaminants dislodged from the chosen allograft product than said extraction fluid; and
   (f) analyzing the extract filtered from the entire amount of the given volume of said extraction fluid for contamination so as to determine contamination of the chosen allograft product;
   wherein during said agitating step, said extraction fluid is contained within an extraction vessel comprising an outer container and a foraminous inner container positioned within said outer container;
   during said agitating step, said allograft products are located within said inner container; and
   said step of removing the allograft products from said extraction fluid comprises removing said inner container from said outer container;
   wherein said agitating step comprises sonicating said extraction fluid at a frequency and duration sufficient to dislodge contaminants from the allograft products while maintaining the viability of any microbial contaminants dislodged from the allograft products and while maintaining the integrity of the allograft products without diminishing biomechanical properties of the allograft products.

2. The method of claim 1, wherein said agitating step comprises sonicating said extraction fluid by applying ultrasonic energy at a frequency of at least about 39 kHz for at least about 1 minute.

3. The method of claim 2, wherein said agitating step comprises sonicating said extraction fluid by applying ultrasonic energy at a frequency ranging from about 39 kHz to about 1 MHz.

4. The method of claim 2, wherein said agitating step comprises sonicating said extraction fluid by applying ultrasonic energy at a frequency ranging from about 39 kHz to about 172 kHz.

5. The method of claim 1, wherein said step of analyzing said extract filtered from the entire amount of the given volume of said extraction fluid for contamination comprises culturing said extract filtered from the entire amount of the given volume of said extraction fluid under conditions suitable for encouraging microbial growth.

6. The method of claim 1, wherein said step of analyzing the extraction fluid for contamination comprises culturing said extract filtered from said extraction fluid.

7. The method of claim 1, wherein said inner container comprises a cylindrical vessel having a plurality of apertures distributed about its surface.

8. The method of claim 1, wherein said inner container comprises a mesh bag.

9. The method of claim 1, wherein said sonicating step comprises:
   (a) providing a sonication bath having a first fluid therein;
   (b) providing a sonication chamber having a second fluid therein, said sonication chamber being sized and configured to receive said outer container therein, and wherein said sonication chamber is positioned at least partially within said first fluid of said sonication bath;
   (c) positioning said outer container within said sonication chamber, such that the level of said second fluid within the sonication chamber is greater than the level of said extraction fluid within the outer container; and
   (d) applying ultrasonic energy to said first fluid in said sonication bath such that the extraction fluid within said outer container is indirectly sonicated.

10. The method of claim 1, wherein said agitating step comprises sonicating said extraction fluid by applying ultrasonic energy at an intensity of at least about 50 Watts per gallon.

11. The method of claim 10, wherein said agitating step comprises sonicating said extraction fluid by applying ultrasonic energy at an intensity ranging from about 50 to about 200 Watts per gallon.

12. The method of claim 10, wherein said agitating step comprises sonicating said extraction fluid by applying ultrasonic energy at an intensity ranging from about 100 to about 550 Watts per gallon.

13. The method of claim 10, wherein said agitating step comprises sonicating said extraction fluid by applying ultrasonic energy at an intensity ranging from about 200 to about 400 Watts per gallon.

14. The method of claim 1, wherein the filter membrane size is selected from a range of about 0.10 μm to about 1.0 μm.

15. The method of claim 1, wherein the filter membrane size is 0.22 μm.

16. The method of claim 1, wherein said step of analyzing the extract filtered from the entire amount of the given volume of said extraction fluid for contamination comprises culturing the extract filtered from the extraction fluid in a single culture.

17. A method of determining contamination of a final allograft product, comprising:
   (a) providing an extraction fluid in a given volume sufficient to fully immerse the final allograft products;
   (b) immersing the final allograft product separate from other allograft products into said extraction fluid;
   (c) agitating said extraction fluid in which the allograft products are immersed so as to dislodge any microbial contaminants from the chosen allograft product;
   (d) removing the final allograft product from said extraction fluid;
   (e) filtering an entire amount of the given volume of the extraction fluid with a filter membrane to produce an extract filtered from the entire amount of the given volume of said extraction fluid, and said extract having a higher concentration of any microbial contaminants dislodged from the final allograft products than said extraction fluid; and (f) analyzing the extract filtered from the entire amount of the given volume of said extraction fluid for contamination so as to determine contamination of the final allograft product;

wherein said agitating step comprises sonicating said extraction fluid at a frequency and duration sufficient to dislodge contaminants from the final allograft products while maintaining the viability of any microbial contaminants dislodged from the final allograft product and while maintaining the integrity of the final allograft product without diminishing biomechanical properties of the final allograft product.

18. The method of claim 17, wherein said step of analyzing the extract filtered from the entire amount of the given volume of said extraction fluid for contamination comprises culturing the extract filtered from the extraction fluid.

19. The method of claim 17, wherein the filter membrane size is selected from a range of about 0.10 μm to about 1.0 μm.

20. The method of claim 17, wherein the filter membrane size is 0.22 μm.

21. The method of claim 17, wherein said step of analyzing the extract filtered from the entire amount of the given volume of said extraction fluid for contamination comprises culturing the extract filtered from the extraction fluid in a single culture.

* * * * *

UNITED STATES PATENT AND TRADEMARK OFFICE
CERTIFICATE OF CORRECTION

PATENT NO.        : 8,158,379 B2                                    Page 1 of 1
APPLICATION NO.   : 10/976078
DATED             : April 17, 2012
INVENTOR(S)       : Chad Ronholdt It is certified that error appears in the above-identified patent and that said Letters Patent is hereby corrected as shown below:

In the Examples, column 8, line 13, "using the swap method" should read --using the swab method--.

Signed and Sealed this
Twenty-ninth Day of May, 2012

David J. Kappos
*Director of the United States Patent and Trademark Office*